US00PP35799P2

(12) United States Plant Patent
Van Swieten

(10) Patent No.: US PP35,799 P2
(45) Date of Patent: May 7, 2024

(54) ***PHALAENOPSIS* ORCHID PLANT NAMED 'PHA308464'**

(50) Latin Name: ***Phalaenopsis* hybrid**
Varietal Denomination: PHA308464

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,131

(22) Filed: Apr. 18, 2023

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
*Assistant Examiner* — Zachariah Allan Kay
(74) *Attorney, Agent, or Firm* — Jondle & Associates, P.C.

(57) ABSTRACT

A new and distinct variety of *Phalaenopsis* plant named 'PHA308464', particularly characterized by white striped flowers with broad reddish-purple edges, and greenish-yellow and white lips, lip callus is even and has a bright color, medium curvature of lateral lobe, and is propagated by meristem tissue culture, is disclosed.

3 Drawing Sheets

Genus and species: *Phalaenopsis* hybrid.
Variety denomination: 'PHA308464'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA308464'.

The new *Phalaenopsis* plant is a product of a planned breeding program conducted by the inventor in Bleiswijk, the Netherlands. The objective of this breeding program was to create a new *Phalaenopsis* plant having numerous attractive, white striped flowers with broad reddish-purple edges, and greenish-yellow and white lips, suitable for potted plant production.

The new *Phalaenopsis* plant 'PHA308464' is a result of cross-pollination made by the inventor in October 2014 in Bleiswijk, the Netherlands, of the proprietary female, or seed parent, *Phalaenopsis* hybrid 'PHALDIMXAP' (U.S. Plant Pat. No. 25,294) with the proprietary male, or pollen parent, *Phalaenopsis* hybrid '11-48223-04' (unpatented).

The new *Phalaenopsis* was selected by the inventor as a single plant within the progeny of the stated cross-pollination in a controlled greenhouse in Bleiswijk, the Netherlands, in August 2017. Asexual reproduction of the new *Phalaenopsis* plant by meristem tissue culture since 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 15, 2021 (Application no. 2021/2268), by Applicant who obtained the subject matter disclosed directly from the inventor. 'PHA308464' has not been made publicly available or sold anywhere in the world prior to the effective filing date of this application with the exception of sales or disclosures made one year or less before the effective filing date of this claimed invention by Applicant who obtained 'PHA308464' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA308464' as a new and distinct variety of *Phalaenopsis* plant:

1) White striped flowers with broad reddish-purple edges, greenish-yellow and white lips;
2) Lip: callus is even and has a bright color; and
3) Lip: curvature of lateral lobe is medium.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2023. Colors in the photographs may differ from the color values cited in the detailed botanical description, which accurately describe the actual colors of the new variety.

DESCRIPTION OF THE NEW VARIETY

Figure 1:
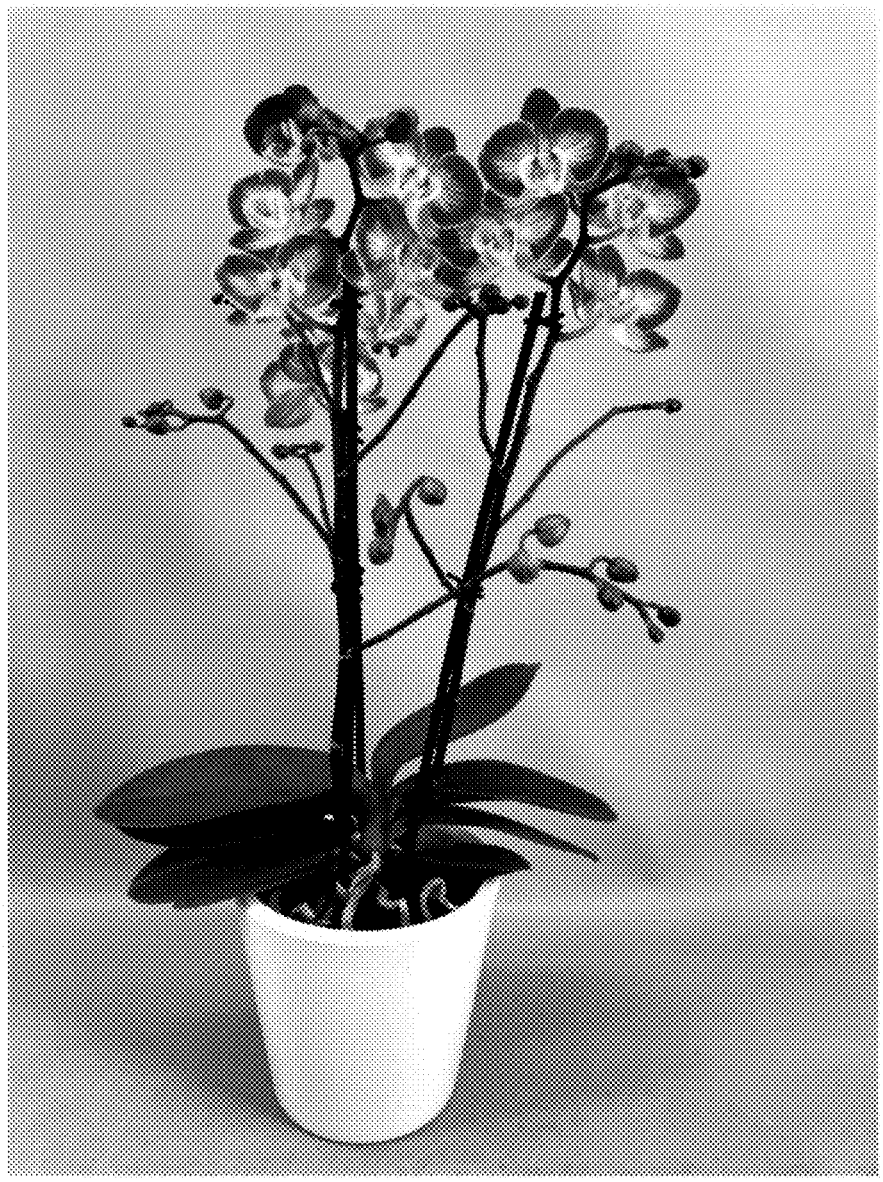
FIG. 1 shows the overall plant habit, including blooms, buds, and foliage of 'PHA308464'.
Figure 2:
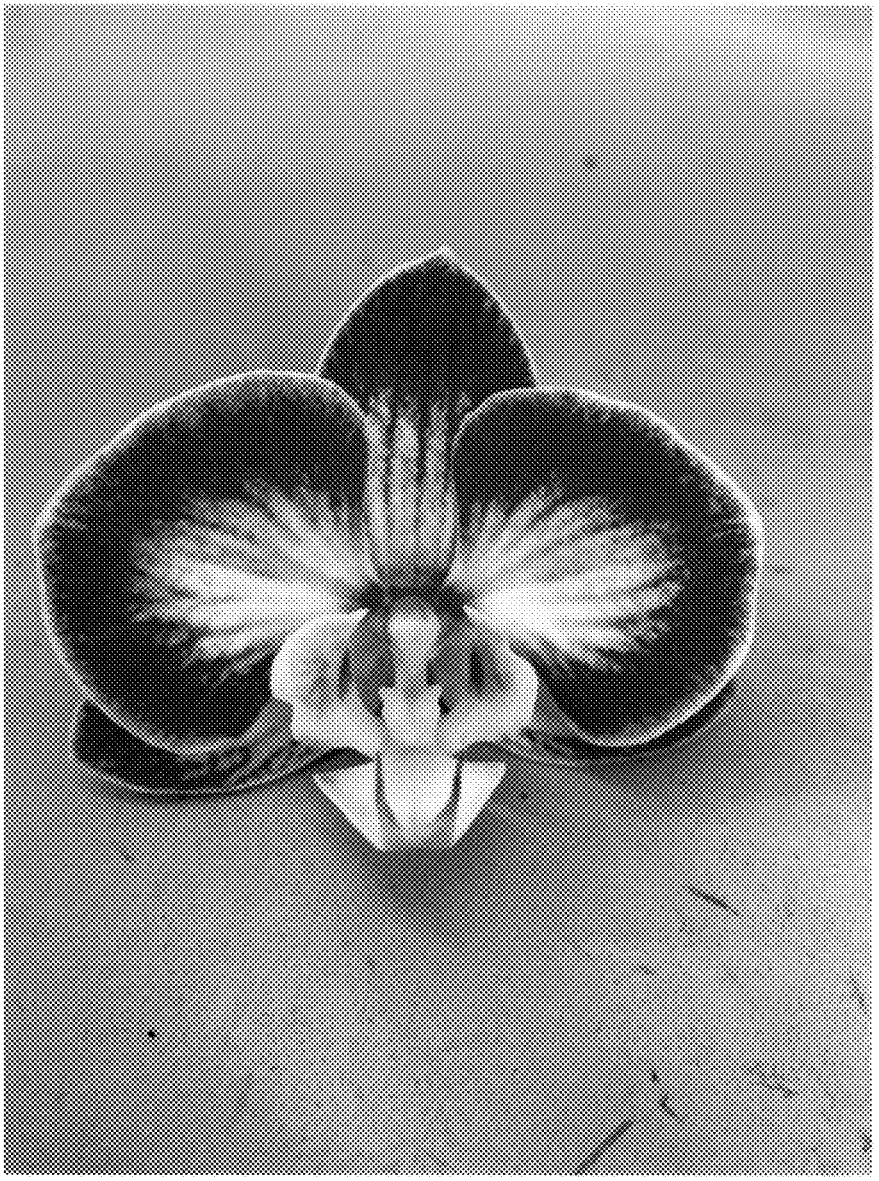
FIG. 2 shows a close-up of a flower of 'PHA308464'.
Figure 3:
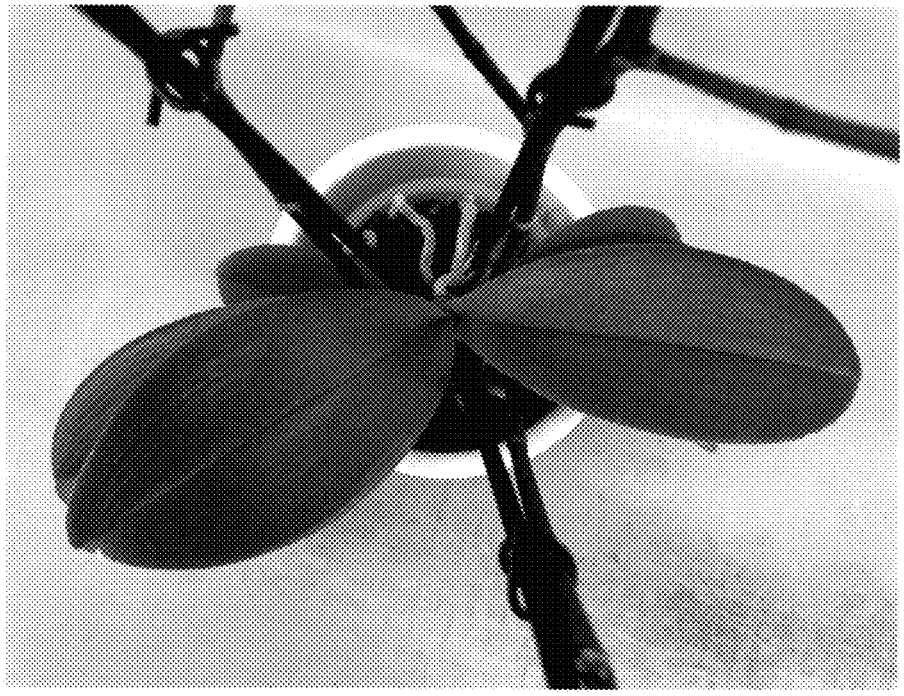
FIG. 3 shows an overhead, close-up view of the leaves of 'PHA308464'.

The following detailed description sets forth the distinctive characteristics of 'PHA308464'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA308464'.

Parentage:

*Female parent*.—*Phalaenopsis* cultivar 'PHALDIMXAP' (U.S. Plant Pat. No. 25,294).

*Male parent*.—*Phalaenopsis* cultivar '11-48223-04' (unpatented).

Propagation:

*Type*.—Meristem tissue culture.

Roots:

*Root description*.—Greyed-green (a color between RHS 190B and 190C) colored roots with branching lateral roots having yellow-green (RHS 144C) with a touch of purplish-red (RHS N77B) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 38.0 cm to 43.0 cm.

*Width* (*measured from leaf tips*).—About 31.0 cm to 33.0 cm.

*Vigor*.—Strong.

Leaves:

*Mature leaves*.—Quantity per plant: 9 to 10 leaves are produced before flowering. Length (fully expanded): 14.0 cm to 16.0 cm. Width: 6.0 cm to 7.0 cm. Position of the broadest part of the leaf: At the middle. Shape: Oblong. Base shape: Moderately elongated. Apex: Obtuse asymmetric. Leaf blade angle with the petiole (measured from the horizontal position): Between 5 degrees and 20 degrees. Leaf margin: Entire. Color: Upper surface: Green (RHS 146A). Lower surface: Green (RHS 146B). Texture (both upper and lower surfaces): Smooth. Thickness: 2.0 mm to 3.0 mm. Variegation: Absent. Venation: Pattern: Parallel. Color of the midvein: Upper surface: Green (RHS 146A). Lower surface: Green (RHS 146B).

Peduncle:

*Quantity per plant*.—3.

*Number of flowers per peduncle*.—16 to 26.

*Length*.—38.0 cm to 43.0 cm.

*Diameter*.—4.0 mm to 5.0 mm.

*Strength*.—Strong.

*Aspect*.—Upright to slightly pendent.

*Texture*.—Smooth.

*Color*.—Green (RHS 146B) with a touch of brown (RHS N200A).

*Internode length*.—1.5 cm to 2.5 cm.

Inflorescence description:

*Appearance*.—Upright to slightly pendent, panicle inflorescence with bilaterally symmetrical flowers that open in succession beginning with the lowermost flower.

*Number of inflorescences*.—3.

*Inflorescence size*.—Height (from base to tip): 230.0 mm to 290.0 mm.

*Flowering time*.—First flowers can be expected 10 to 11 months after planting in a 12-cm pot.

*Flower*.—Height: 50.0 mm to 55.0 mm. Diameter: 65.0 mm to 70.0 mm. Depth of lip: 19.0 mm to 21.0 mm.

*Flower longevity*.—On the plant: 12 to 14 weeks.

*Flower shape in lateral view*.—Flat.

*Fragrance*.—Absent.

*Flower bud*.—Average size: Medium. Length: 16.0 mm to 18.0 mm. Width: 13.0 mm to 15.0 mm. Shape: Egg shaped. Color: Light yellow-green (RHS 145B) with a touch of reddish-purple (RHS N78B) toward the tip.

*Petals*.—Arrangement: Open/free. Shape: Semi-circular. Apex: Obtuse. Margin: Weakly undulated. Length (from base to tip): 28.0 mm to 30.0 mm. Width: 34.0 mm to 36.0 mm. Position of the broadest part of the petal: Toward the base. Color (when fully opened): Upper surface: Basic color: White (RHS NN155C). Over color: Very light purple shade (RHS 76B) on one side from the base; reddish-purple (RHS N78B) toward the margin; reddish-purple (RHS N78A) stripes. Lower surface: Basic color: White (RHS NN155C). Over color: Light reddish-purple (RHS N78D) toward the margin; diluting light purple stripes (RHS 76A). Number of spots and stripes on the petals (upper surface): Several stripes. Color of spots and stripes on the petals (upper surface): RHS N78A. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 31.0 mm to 33.0 mm. Width: 22.0 mm to 24.0 mm. Position of the broadest part of the dorsal sepals: At the middle. Color (when fully opened): Upper surface: Basic color: Very light purple (RHS 76B). Over color: Reddish-purple (RHS N78B) toward the margin; reddish-purple stripes (RHS N78A). Lower surface: Basic color: Very light purple (RHS 76C). Over color: Touch of light yellow-green (RHS 145D) and light reddish-purple (RHS N78D). Number of spots and stripes on the dorsal sepals (upper surface):

Several stripes. Color of spots and stripes on the dorsal sepals (upper surface): RHS N78A. Density of netting of the dorsal sepals (upper surface): Low. Color of the netting: RHS N78A.

*Lateral sepals*.—Shape: Ovate. Apex: Obtuse asymmetric. Margin: Entire. Length (from base to tip): 32.0 mm to 34.0 mm. Width: 19.0 mm to 21.0 mm. Position of the broadest part of the lateral sepals: Toward the base. Color (when fully opened): Upper surface: Basic color: White (RHS NN155C). Over color: Touch of light yellow-green (RHS 145C) at the base; purplish-pink (RHS N78C) toward the tip; reddish-purple stripes and netting (RHS N78A). Lower surface: Basic color: White (RHS NN155C). Over color: Light yellow-green (RHS 145C) at the base; light reddish-purple (RHS N78D) toward tip; diluting light purple stripes (RHS 76A). Number of spots and stripes on the lateral sepals (upper surface): Few to medium stripes. Color of spots and stripes on the lateral sepals (upper surface): RHS N78A. Density of netting of the lateral sepals (upper surface): Low. Color of the netting (upper surface): RHS N78A.

*Labellum* (*lip*).—Whiskers: Present. Length of whiskers: 7.0 mm to 8.0 mm. Color of whiskers: Reddish-purple (RHS N78B) with small white tips (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Weakly undulated. Length: 17.0 mm to 19.0 mm. Width: 12.0 mm to 14.0 mm. Color: Upper surface: Greenish-yellow (RHS 3B) at the base; white (RHS NN155C) with purplish-red stripes (RHS N78C) at the middle. Lower surface: Light yellow-green (RHS 3B) at the base; greenish-yellow (RHS 3B) on one side; light purple (RHS 76A) toward tip. Number of spots and stripes on the lateral lobe: Few stripes. Color of spots and stripes on the lateral lobe: RHS N78C. Density of netting of the lateral lobe: None. Color of the netting: None.

*Apical lobe*.—Shape: Triangular. Margin: Entire. Length: 18.0 mm to 20.0 mm. Width: 15.0 mm to 17.0 mm. Color: Upper surface: Greenish-yellow (RHS 6A) at the middle at the base; light greenish-yellow (RHS 5C) toward wings; white (RHS NN155C) toward whiskers with a touch of purplish-pink (RHS N78C). Lower surface: Greenish-yellow margin (RHS 5B) and light yellow-green (RHS 157C) at the base with a touch of RHS 145C at the middle from the base; very light purple (RHS 76C) toward whiskers. Number of spots and stripes on the apical lobe: None. Color of spots and stripes on the apical lobe: None. Density of netting of the apical lobe: None. Color of the netting: None.

*Callus*.—Average size: Medium. Height: 5.0 mm to 6.0 mm. Length: 5.0 mm to 6.0 mm. Width: 4.0 mm to 5.0 mm. Color: Light greenish-yellow (RHS 5C) front and greenish-yellow tips (RHS 5A); light greenish-yellow (RHS 1D) on sides.

Reproductive organs:

*Column*.—Length: 9.0 mm to 10.0 mm. Diameter: 4.0 mm to 5.0 mm. Color: Reddish-purple (RHS N78B).

*Pollinia*.—Quantity: 2. Diameter: 0.9 mm to 1.1 mm. Color: Orange-yellow (RHS 23A).

*Ovary*.—Length: 10.0 mm to 12.0 mm. Diameter: 2.4 mm to 2.6 mm.

*Pedicel*.—Length: 31.0 mm to 33.0 mm. Diameter: 2.7 mm to 3.0 mm. Texture: Smooth. Color: Light yellow-green (RHS 145A) at the base; lighter yellow-green (RHS 145B) with a touch of very light purple (RHS 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA308464' differs from the female parent plant 'PHALDIMXAP' (U.S. Plant Pat. No. 25,294), in that 'PHA308464' has white petals, white apical lobes, and obtuse dorsal sepal apexes, whereas 'PHALDIMXAP' has reddish-purple petals, dark red apical lobes, and rounded dorsal sepal apexes.

'PHA308464' differs from the male parent plant '11-48223-04' (unpatented) in that 'PHA308464' has reddish-purple columns, trullate apical lobes, and obtuse dorsal sepal apexes, whereas '11-48223-04' has white columns, triangular apical lobes, and emarginated dorsal sepal apexes.

'PHA308464' is most similar to the commercial *Phalaenopsis* plants named 'PHALIPUE' (U.S. Plant Pat. No. 33,312) and 'PHALARALS' (U.S. Plant Pat. No. 33,097). 'PHA308464' differs from the commercial variety 'PHALIPUE' in that 'PHA308464' has narrow to medium flowers, obtuse apexes, and whiskers that are reddish-purple with small white tips, whereas 'PHALIPUE' has medium flowers, emarginated apexes, and whiskers that are light purple with greenish-yellow tips. Additionally, 'PHA308464' has shorter whiskers than 'PHALIPUE'.

'PHA308464' differs from the commercial variety 'PHALARALS' in that 'PHA308464' has an even callus pattern, obtuse apexes, and narrow to medium flowers, whereas 'PHALARALS' has a dotted callus pattern, emarginated apexes, and medium to broad flowers.

I claim:

1. A new and distinct variety of *Phalaenopsis* plant named 'PHA308464', substantially as described and illustrated herein.

* * * * *